United States Patent [19]

Kishimoto et al.

[11] Patent Number: 5,266,719
[45] Date of Patent: Nov. 30, 1993

[54] METHOD OF PREPARING α-L-ASPARTYL-L-PHENYLALANINE METHYL ESTER

[75] Inventors: Shinichi Kishimoto; Kimiyasu Sakamoto; So Abe; Toshihisa Kato, all of Kawasaki, Japan

[73] Assignee: Ajinomoto Co., Inc., Tokyo, Japan

[21] Appl. No.: 885,766

[22] Filed: May 20, 1992

[30] Foreign Application Priority Data

May 23, 1991 [JP] Japan .................................. 3-221334

[51] Int. Cl.$^5$ .......................................... C07C 229/00
[52] U.S. Cl. ......................................... 500/41; 560/40; 560/38
[58] Field of Search .............................. 560/38, 40, 41

[56] References Cited

FOREIGN PATENT DOCUMENTS 0099960 2/1984 European Pat. Off. .
63-145298 6/1988 Japan .
WO83/01619 5/1983 PCT Int'l Appl. .

OTHER PUBLICATIONS

Chemical Abstracts, 66803b, vol. 79, No. 11, Sep. 17, 1973, p. 484, & Bull. Chem. Soc. Jap., (1973), 46(6), pp. 1893-1895.
Y. Ariyoshi, et al., "Synthesis of a Sweet Peptide, α-Aspartyl-L-Phenyl-Alanine Methyl Ester, Without the use of Protecting Groups".
Chemical Abstracts, 6056z, vol. 85, No. 1, (Jul. 5, 1976), p. 492, & JP-A2-76-13 737, Feb. 3, 1976, N. Uchiyama, et al., "α-Aspartyl-L-Phenylalanine Lower Alkyl Esters".
Chemical Abstracts, 136391g, vol. 87, No. 17, Oct. 24, (1977), p. 800, & JP-A2-76-95 017, Aug. 20, 1976, M. Fujino, et al., "Aspartyl Dipeptide Esters".

*Primary Examiner*—Jose' G. Dees
*Assistant Examiner*—Keith MacMillan
*Attorney, Agent, or Firm*—Oblon, Spivak, McClelland, Maier & Neustadt

[57] ABSTRACT

In neutralizing an acid addition salt of α-APM in an aqueous medium, the α-APM concentration in the neutralized liquid is controlled to fall within the range of from 3 to 10 wt. % at the finish of neutralization. Then, the liquid is heated to 50° to 80° C. and neutralization is effected with stirring to the isoelectric point of α-APM; or after the neutralization, the neutralized liquid is heated. The neutralized liquid is thereafter cooled with or without stirring so that crystals of α-APM are precipitated.

10 Claims, No Drawings

METHOD OF PREPARING α-L-ASPARTYL-L-PHENYLALANINE METHYL ESTER

BACKGROUND OF THE INVENTION

1. Field of the Invention

The present invention relates to a method of preparing α-L-aspartyl-L-phenylalanine methyl ester (α-APM) which is useful as a sweetener and more specifically to an improved method of preparing α-APM by neutralizing an acid addition salt of α-APM with a base.

More precisely, it relates to a method of neutralizing an acid addition salt of α-APM in an aqueous medium, where the neutralization is effected under particular concentrations and particular temperature conditions and is followed by cooling to cause crystallization of α-APM.

2. Discussion of the Background

α-APM of the present invention is a dipeptide sweetener having a sweetness of about 200 times that of sucrose (cane sugar). Because of its good quality sweetness and low calory content, it has become widely used as a diet sweetener, and the worldwide demand for it is estimated to be over 10,000 tons by 1995.

α-APM is produced industrially by several methods. In one method, an N-substituted aspartic acid anhydride and a phenylalanine methyl ester are reacted and bonded together in an organic solvent and the N-substituent is then removed from the product (U.S. Pat. No. 3,786,039). A second method of obtaining α-APM is to methyl-esterify α-L-aspartyl-L-phenylalanine in a mixed solvent comprising water, methanol and hydrochloric acid to obtain α-APM hydrochloride, and then neutralize the salt to obtain α-APM (Japanese Patent Application Laid-Open No. 53-82752). A third method of obtaining α-APM is to condense an N-substituted aspartic acid and a phenylalanine methyl ester in the presence of an enzyme and then remove the N-substituent from the product (Japanese Patent Application Laid-Open No. 55-135595).

In the first chemical synthetic method noted above, the β-isomer (β-L-aspartyl-L-phenylalanine methyl ester) is produced as a side product. As a means of selectively removing impurities including the β-isomer, a purification method is used in which α-APM containing impurities is brought into contact with a hydrohalogenic acid and then subjected to solid-liquid separation to isolate α-APM as its hydrohalide salt.

Where industrial scale production of α-APM is required to meet the current demands, chemical methods are the major methods from the viewpoint of reducing the manufacturing cost. In this case, esterification is often effected via its hydrochloride salt as in the second method noted above, or after formation of α-APM, the hydrohalide salt is formed and purified as described above. To obtain α-APM from its hydrohalide salt, such as its hydrochloride salt, using an ordinary method, the hydrohalide salt of α-APM is dissolved or suspended in an aqueous medium and the resulting solution or suspension is neutralized by adding an aqueous solution of a base such as sodium hydroxide, sodium hydrogen carbonate or ammonia.

However, the present inventors have discovered that when a large amount, over a liter scale, of liquid must be dealt with during an industrial scale neutralization operation, such as the neutralization of an acid addition salt of α-APM, the conventional neutralization method has serious problems.

Specifically, when a base is continuously added dropwise to an aqueous solution of an acid addition salt of α-APM to reach the isoelectric point of α-APM, rapid precipitation of α-APM occurs during the course of the addition so that stirring of the system becomes impossible. In the worst case, it has been found that the stirrer completely stops. If the amount of liquid is at most 100 ml or so, as in a laboratory scale experiment, the precipitated solid phase can be easily broken with a tool, such as a spatula, whereby the fluid condition can be recovered. However, when the amount of liquid is large, i.e., about a liter or more, for example, in a bench plant or the like, or where the neutralization is carried out in a large-scale pilot plant or commercial plant, this method can not be used for solving the problem.

As a countermeasure to this problem in an industrial scale neutralization, addition of a large amount of water may be considered so as to carry out the neutralization using a diluted concentration. However, this lowers the capacity and efficiency of the device used and also lowers the yield of the product. Therefore, dilution is not a good countermeasure.

On the other hand, very slow addition of an aqueous base solution over an extremely long period of time would be effective for ensuring the fluidity of the liquid, but is ineffective from the view point of the production. Still another method is intermittently discontinuing the dropwise addition of the neutralizing agent into the reaction system having a pH range at which precipitation of α-APM starts or a pH value of 2.5 or so, to ripen the precipitated crystals (Japanese Patent Application Laid-Open No. 63-145298). This method has the serious drawback that the pH range suitable for the ripening fluctuates greatly unless the initial concentration of α-APM (or its acid addition salt) is strictly controlled to certain values. The α-APM content in the separated wet crystals (acid addition salt) always fluctuates, depending upon the delicate conditions occurring during the crystallization of the acid addition salt of α-APM. It is difficult, therefore, to keep the initial concentration of α-APM (or its acid addition salt) constant in a dissolution system controlling the amounts of liquid often used in industrial production.

In order to avoid this problem, a complicated concentration control system is necessary to effect batch-wise analysis every time and then to supply crystals or water when needed. Alternatively an expert monitor skilled in the art must be exclusively dedicated to the system to be able to batchwise determine the suitable ripening pH value each time.

Finally, even though these operational problems can be avoided by any of the above-mentioned systems, the α-APM crystals obtained still have extremely poor solid-liquid separability, which requires increased equipment costs and increased energy consumption in the filtration and drying steps used as the post-treatment steps.

A need continues to exist for a method of overcoming the above-mentioned problems in neutralizing an acid addition salt of α-APM.

SUMMARY OF THE INVENTION

Accordingly, one object of the present invention is to provide a method for overcoming the problems associated with neutralizing an acid addition salt of α-APM.

This and other objects which will become apparent from the following specification have been achieved by the present process.

In the present method, when dissolving an acid addition salt of α-APM in an aqueous medium, the α-APM concentration in the solution at the finish of neutralization is controlled to fall within a particular range and thereafter the solution is heated to an elevated temperature and subjected to neutralization up to the isoelectric point of α-APM with stirring, then the resulting neutralized liquid is cooled to cause precipitation of crystals of α-APM.

Cooling of the neutralized liquid may subsequently be effected under conditions of forced flow, for example, with stirring to obtain a crystal suspension having fluidity, which is generally called a slurry. Alternatively, cooling may also be effected rapidly with extremely slow stirring or without stirring to obtain all or a part of the liquid as a non-fluid sherbet-like pseudosolid phase. It has been found that the latter is more effective from the viewpoint of improving the operability of the process and the solid-liquid separability of the crystals formed.

For improving the filterability of the crystals formed, it has been found that the main reason for poor filterability is the crystallization inhibiting effect of coexisting impurities, such as salts formed by neutralization. Therefore, before initiating cooling, α-APM having a relatively high purity is preferably added to the neutralized liquid to reduce the relative concentration of the impurities. De-salting by recrystallization or electric dialysis or with a reverse osmotic membrane may also be used prior to cooling, whereby noticeable improvement of the filterability of the crystals formed is attained. In addition, it has also been found that the powdery properties of the dried final product are improved noticeably.

DETAILED DESCRIPTION OF THE PREFERRED EMBODIMENTS

The process of the present invention drastically reduces the necessary equipment and energy costs and reduces the number of personnel necessary for carrying out the neutralization and crystallization process.

Specifically, the present invention is a method of preparing α-APM by neutralizing an acid addition salt of α-APM with a base to the isoelectric point, such that in an aqueous medium, (a) the concentration of α-APM is controlled to fall within the range of from 3 to 10 wt. % at the end of neutralization, (b) the neutralization is effected at a liquid temperature falling within the range of from 50° to 80° C. with stirring, and (c) the resulting neutralized liquid is cooled so that crystals of α-APM are precipitated out.

Acid addition salts of α-APM which are usable in the present invention include mineral acid salts, such as hydrochloride, hydrobromide, sulfate and phosphate salts. The hydrochloride salt is preferred.

In the present invention, an acid addition salt of α-APM is neutralized in the form of an aqueous solution or suspension. As the solvent, water is suitable or a mixed solvent comprising a water-miscible organic solvent and water may be used. Since the solubility of α-APM (acid addition salt) temporarily increases with neutralization, all the acid addition salt crystals need not be dissolved at the start of neutralization.

Suitable base neutralizing agents, include alkali hydroxides such as sodium hydroxide, alkali carbonates or bicarbonates such as sodium carbonate and bicarbonate, ammonia and other organic amines, preferably $C_{1-10}$ monoalkyl and dialkyl amines. From the viewpoint of prevention of decomposition of α-APM during neutralization as well as cost and easy operability, sodium carbonate or ammonia are frequently used, where ammonia is in the form of its aqueous ammonium hydroxide solution. The amount of the base used is the amount necessary to bring the solution of the acid addition salt of α-APM to the isoelectric point of α-APM.

During neutralization, close attention must be paid to determination of the operating temperature and the α-APM concentration, including consideration of the added increment of water resulting from addition of the neutralizing agent. That is to say, if the concentration is too low, the yield in the crystallization will be low. When the initial concentration is 3 wt. % or less as α-APM in crystallization, the filterability of the crystals formed rapidly worsens. Therefore, the α-APM concentration at the beginning of crystallization must be 3 wt. % or more and the operating temperature must be 50° C. or higher at which almost no precipitation of crystals occurs.

On the other hand, if the concentration is too high, excess crystals precipitate during neutralization. Though precipitation of a small amount of crystals at the end of neutralization does not noticeably interfere with the advantages of the present invention, it is preferred that no crystals precipitate at the end of neutralization or at least at the start of crystallization, to obtain the best effects of the present invention and highest yields.

When the α-APM concentration is set high at the start of crystallization, the liquid temperature must also be high in accordance with the high α-APM concentration. However, α-APM has stability problems when it is in the dissolved form in an aqueous medium. That is, an aqueous α-APM solution can form α-L-aspartyl-L-phenylalanine (α-AP) by hydrolysis or a diketopiperazine compound (DKP) by an intramolecular cyclization reaction under high temperature conditions. Such decomposition reactions lower the yield and quality of the product and are therefore unfavorable in production of the product. From the viewpoint of inhibiting the decomposition, the upper limit of the temperature is preferably 80° C. and the upper limit of the α-APM concentration is preferably 10 wt. % or less which is the solubility at that temperature.

In a low pH range where a large amount of free acid is present during the course of neutralization, α-AP is often formed by hydrolysis under high temperature conditions. In this case, therefore, it is desired that the liquid temperature be 40° C. or lower until the pH value is slightly above the isoelectric point of the acid addition salt of α-APM (for instance, in the case of hydrochloride, pH of 2.5 or so). Since the solubility in the vicinity of the isoelectric point of the acid addition salt of α-APM is noticeably high (for instance, in the case of α-APM hydrochloride, a solubility of 10 wt. % or more at a temperature of 30° C.), there is no danger of precipitation of crystals at this stage. Afterwards, neutralization may be effected continuously up to the isoelectric point of α-APM during or after elevation of the temperature.

Where an aqueous sodium carbonate solution or the like is used as a neutralizing agent, it is preferred to keep the neutralized liquid in a high temperature within the preferred range to reduce decomposition of α-APM after neutralization, since higher temperatures promote release of carbon dioxide gas from the liquid and make the operation of the crystallization step easier.

In the crystallization step, the same apparatus as that used in the neutralization step may be used. However, from the viewpoint of the materials constituting the apparatus, employment of another apparatus made of different lower quality materials would be preferred to save plant cost. For instance, stirring tank, draft tube baffle or crystal-Oslo crystallizers as well as modifications of these, which are widely and popularly used as industrial crystallizers, can be used. Such crystallizers can be driven under forced flow conditions, in accordance with their intrinsic operation, whereby a fluid crystal floating suspension (slurry) is obtained by cooling.

The present method is superior to other methods where crystals are precipitated out directly by neutralization due to the easy operation of the process and the good filterability of the crystals formed. In order to further improve the process, cooling is desirably effected without stirring or with intermittent stirring or under a weak forced flow whereby the whole or a part of the neutralized liquid is obtained as a sherbet-like pseudosolid phase. In this cooling process, however, the time necessary for cooling is longer than when effecting a sufficient forced flow and, in addition, the inside of the crystallizer has a temperature distribution. Therefore, from the viewpoint of inhibition of decomposition of $\alpha$-APM and yield, the maximum distance between the substance to be cooled and the cooling surface in the crystallizer should be small. The above-mentioned conventional industrial crystallizers can be used with no stirring or with weak stirring or intermittent stirring, but more preferably, the crystallizing apparatus has a sufficient large heat transfer surface to ensure adequate liquid volume and to ensure that the maximum distance between the substance to be cooled and the cooling surface is 500 mm or less. After formation of the pseudosolid phase, cooling may be continued as is and/or the pseudosolid phase formed may be broken under the conditions of forced flow and, if desired, cooling further effected, whereupon the residual $\alpha$-APM remaining in the mother solution is recovered.

In accordance with the present method, almost all of the problems of the neutralization step for neutralizing an acid addition salt of $\alpha$-APM and the crystallization step for forming crystals of $\alpha$-APM are overcome. In addition, the solid-liquid separability of the finally obtained $\alpha$-APM crystals, as well as the powdery properties of the dried product, are noticeably improved by selectively removing impurities present in the prestep before crystallization.

Salts formed by neutralization are a serious impurity which interfere with the growth of crystals of $\alpha$-APM. Various salts are formed by neutralization, depending upon the kinds of the acids and bases used. For instance, where hydrochloric acid is used as an acid and sodium carbonate is used as a base, sodium chloride is formed; and where hydrobromic acid is used as an acid and ammonia is used as a base, ammonium bromide is formed. All of these salts have about the same severe effect, interfering with crystallization of $\alpha$-APM. For instance, when only about 1 wt. % of such a salt is in the liquid to be crystallized, it will have an influence on the growth of crystals of $\alpha$-APM during crystallization.

Recrystallization is effective to selectively remove such salts and other impurities. Preferably, the crystals obtained by the first crystallization conducted directly after neutralization, are again dissolved in a hot aqueous medium and the resulting solution is cooled to precipitate crystals. In both the first crystallization and the second crystallization, any of the above-mentioned crystallization apparatus and methods may be employed. Preferably, however, the method of forming a sherbet-like pseudosolid phase is employed for at least the second crystallization.

It is also effective to subject the neutralized liquid to Ruth's reverse osmotic membrane treatment or electric dialysis treatment to desalt the liquid, since the crystallization may be finished in one operation. In this case, desalting of the neutralized liquid and concentration may be carried out simultaneously, and the final $\alpha$-APM concentration may naturally fall within the range of from 3 to 10 wt. %. If necessary, the concentration may be lower than the concentration range at the end of neutralization. Desalting is preferably conducted in such a way that at least 50 wt. % or more of salts existing at the start of the crystallization operation are removed, in view of improvement of the solid-liquid separability of the crystals formed.

Improvement of the crystal properties of $\alpha$-APM may also be effected without removing salts from the system. The problem of salt impurities is a function of the relative ratio of the $\alpha$-APM to impurity concentration in the system. Therefore, where a solution of $\alpha$-APM having a relatively high purity and/or crystals thereof are added to the neutralized liquid (or solution of $\alpha$-APM acid addition salt) before during or after neutralization, and if desired, water is added, then blended and dissolved to form a solution having an $\alpha$-APM concentration of from 3 to 10 wt. %, problems associated with the presence of the salts is minimized. The resulting solution is then cooled for crystallization.

$\alpha$-APM to be added may be obtained from any source. Preferably, a portion of $\alpha$-APM crystals obtained by the method of the present invention is used as the additional $\alpha$-APM component. While the crystals are still in a wet condition, they may be used for neutralization of an acid addition salt of $\alpha$-APM in the next batch. The amount of such $\alpha$-APM crystals may be larger to obtain a greater effect. From the viewpoint of the producibility, however, it is suitably not higher than the same molar amount as the acid addition salt of $\alpha$-APM to be neutralized.

In the method of the present invention for preparing $\alpha$-APM by neutralizing an acid addition salt of $\alpha$-APM with a base on an industrial scale, especially a liter scale or larger, the properties of the liquid, such as the fluidity during neutralization, are greatly improved and the solid-liquid separatability of the $\alpha$-APM crystals produced, as well as the powdery, characteristics of the dried product, are also noticeably improved. Additionally, the steps constituting the method are simplified. Therefore, the method of the present invention is extremely valuable as an industrial method.

Other features of the invention will become apparent in the course of the following descriptions of exemplary embodiments which are given for illustration of the invention and are not intended to be limiting thereof.

EXAMPLES

The test for evaluating the filterability of $\alpha$-APM crystals obtained in the examples was conducted by the method described below.

Method of Measuring Filtration Specific Cake Resistance

One liter of a sample is filtered through a top-feed system suction filter (leaf tester). The pressure difference during filtration was 70 mmHg, which was kept constant throughout the filtration. From the start of filtration, the amount of the filtrate V(cm$^3$) was measured at regular intervals and plotted on a graph having the amount of the filtrate as the horizontal axis and the value ($\theta$/V), obtained by dividing time of filtration $\theta$ (sec) by the amount of the filtrate, as the vertical axis. The slope of the line K (sec/ml$^2$) is obtained by the least squares method. The value C′, obtained by dividing the total amount (g) of the crystals in the slurry by the total amount (cm$^3$) of the liquid in the slurry, is used in the following equation for specific cake resistance. The filtration area A was 93 (cm$^2$); and the viscosity $\mu$ of the filtrate was 0.0135 (g/cm.sec). The specific cake resistance $\alpha$ thus calculated is a measure of the filterability of the sample. Samples having a lower value $\alpha$ are more easily filtered.

Equation for Specific Cake Resistance $$\alpha = 20 \cdot K \cdot A^2 \cdot PT/\mu \cdot C'(m/kg)$$

where $\alpha$ is the specific cake resistance (m/kg) of the filtered cake;

$\mu$ is the viscosity of the filtrate (g/cm.sec);

PT is the pressure difference (dyne/cm$^2$) of the filtered cake and the filtration device = $\Delta P$(mmHg) × 1333.22;

A is the filtration area (cm$^2$); and

C′ is the weight of the crystals per unit volume of the liquid component in the slurry (g/cm$^3$) = dry cake weight (g)/(wet cake weight (g) − dry cake weight (g) + amount of final filtrate (cm$^3$)).

EXAMPLE 1

1900 ml of ion-exchanged water was put in a 2-liter jacketed flask having an inner diameter of 125 mm and was stirred at 250 rpm with an anchor-type stirrer having a blade diameter of 10 cm. The inside temperature of the flask was kept at 27° C. by circulating warm water through the jacket, and 150 g of wet crystals of APM hydrochloride were dissolved. To this was added 150 mM Na$_2$CO$_3$ aqueous solution so that the liquid blend was adjusted to have pH of 2.5 and then heated to 55° C. The solution was then adjusted to have pH of 4.9 with Na$_2$CO$_3$ aqueous solution and was heated to 65° C. The $\alpha$-APM concentration was 4.2 g/dl. With continuous stirring at 250 rpm, stirring crystallization was effected while cooling water at 5° C. was introduced into the jacket. Cooling was continued until the temperature of the system became 9° C. During the course of cooling, no change for the worse of the stirring condition by deposition of crystals was noticed and good operation was ensured throughout the cooling procedure. Thus, a slurry with good solid-liquid separatability was obtained, having a specific cake resistance of 4.6 × 10$^{10}$ m/kg.

COMPARATIVE EXAMPLE 1-1

The same apparatus as used in Example 1 was used and stirring was conducted at 250 rpm. The inside apparatus temperature was kept at 27° C. by introducing warm water into the jacket, and 240 g of wet crystals of APM hydrochloride o were dissolved in 1900 ml of water. The $\alpha$-APM concentration was 7.3 g/dl. While the solution was maintained at a temperature of 27° C., 16 wt. % sodium carbonate was added dropwise thereto at a constant rate (7 ml/min). The scheduled time before the finish of neutralization (pH 4.9) was 30 minutes, but the liquid lost fluidity with deposition of crystals (pH 3.0, after 16 minutes), and the stirring stopped in 21 minutes after the start of the experiment. The content in the flask was solidified.

COMPARATIVE EXAMPLE 1-2

Using the same apparatus as used in Example 1, 150 g of crystals of APM hydrochloride were dissolved in 1900 ml of water and heated to 28° C. The solution contained 4.6 g/dl of $\alpha$-APM. With stirring at 400 rpm, 130 ml of 150 mM Na$_2$CO$_3$ aqueous solution was added dropwise to the solution with a micro-pump over a period of 6 hours so that the solution was neutralized to have a final pH of 4.9. Rapid deposition of crystals occurred when the pH of the solution became about 3.1 and stirring of the liquid became difficult, and could barely be accomplished. After cooling to 9° C., the obtained slurry was dewatered in a centrifugal separator having a diameter of 4.7 inches at 3800 rpm for 5 minutes. Handling of the slurry was extremely difficult, and the slurry had a specific cake resistance of 1.1 × 10$^{11}$ m/kg. The moisture content in the crystals was 65 wt. %.

EXAMPLE 2

1900 ml of ion-exchanged water was put in a 2-liter jacketed flask having an inner diameter of 125 mm, and was stirred at 250 rpm with an anchor-type stirrer. The inside temperature of the flask was maintained at 28° C. by circulating warm water into the jacket, and 150 g of wet crystals of APM hydrochloride were dissolved.

To this was added 150 mM Na$_2$CO$_3$ aqueous solution so that the liquid mixture was adjusted to have a pH of 2.5 and then heated to 55° C. The solution was then adjusted to have a pH of 4.9 with Na$_2$CO$_3$ aqueous solution and was heated to 65° C. The $\alpha$-APM concentration was 4.6 g/dl. After the stirring was stopped, cooling water at 5° C. was introduced into the jacket. Cooling was continued without stirring, and the whole mass of the neutralized liquid became a sherbet-like phase. Next, this was stirred at 200 rpm and cooling was continued further until the inner temperature of the system became 7° C. The slurry thus obtained was dewatered in a centrifugal separator having a diameter of 4.7 inches at 3800 rpm for 5 minutes. The slurry was extremely good, having a specific cake resistance of 2.8 × 10$^9$ m/kg. Separatability of the crystals formed was also good, having a moisture content of 47 wt. %.

EXAMPLE 3

1900 ml of an aqueous solution of APM hydrochloride was put in the same apparatus as used in Example 2, and 28 % NH$_4$OH was added thereto with stirring at 200 rpm at 27° C. so that the solution was adjusted to have a pH of 3.0. The solution was heated to 55° C. and 28 % NH$_4$OH was added thereto to obtain a pH of 4.9. The decolored liquid contained 4.2 g/dl of $\alpha$-APM. After the stirring was stopped, cooling water at 5° C. was introduced into the jacket so as to cool the system. A sherbet-like phase formed completely on the inside of the flask. After 50 minutes, stirring was again started at 200 rpm and cooling was continued until the inner temperature became 7.5° C. The slurry thus obtained was dewatered in a centrifugal separator having a diameter of 4.7 inches at 3800 rpm for 5 minutes.

The slurry had good solid-liquid separatability, having a specific cake resistance of $3.1 \times 10^9$ m/kg and a moisture content in the crystals of 46 wt. %.

COMPARATIVE EXAMPLE 2

Using the same apparatus as used in Example 2, 65 g of crystals of APM hydrochloride were dissolved in 1760 ml of water. The solution was neutralized in the same manner as in Example 2 with 150 mM $Na_2CO_3$ aqueous solution and then decolorized with activated charcoal. The solution was determined to contain 2.4 g/dl α-APM. The aqueous solution was heated to 68° C. for one hour. Then the stirring was stopped and cooling water at 5° C. was introduced into the outer jacket to conduct static crystallization. Cooling was continued for 3 hours without stirring, then stirring was effected at 200 rpm and cooling was continued further until the inner temperature became 7° C. The slurry thus obtained was dewatered in a centrifugal separator having a diameter of 4.7 inches at 3800 rpm for 5 minutes. The slurry was much worse than that obtained in Example 2, the former having a specific cake resistance of $1.3 \times 10^{10}$ m/kg and a crystal moisture content of 72 wt. %.

EXAMPLE 4

This demonstrates a 400-liter scale experiment. Twenty four kg of APM hydrochloride crystals were dissolved in 320 liters water and heated to 36° C. With stirring, 1.3 liters of 28 wt. % $NH_4OH$ aqueous solution was added thereto, whereby the resulting solution was adjusted to have a pH of 2.5. This solution was further heated to 65.5° C., and 3.0 liters of 28 wt. % $NH_4OH$ aqueous solution was added thereto to obtain a pH of 4.9. The aqueous solution contained 4.9 g/dl of α-APM and this was transferred into a jacketed cylindrical crystallizer having an inner diameter of 400 ml and a total length of 3000 mm. The crystallizer had no stirring equipment. Cooling water of −5° C. was introduced into the jacket for 3.5 hours. The bottom of the crystallizer was then opened and the content was transferred into another crystallizer equipped with a stirring equipment. This was continuously cooled overnight with stirring until the temperature thereof became 5° C. The bottom of the crystallizer was opened and the crystals were taken out. Scaling on the inner wall of the crystallizer was not observed and the crystal slurry was easily removed. 350 liters of the slurry thus obtained was subjected to solid-liquid separation in a centrifugal separator having a diameter of 36 inches and a volume of 92 liters, whereupon only 3 minutes were needed for charging the slurry into the separator. The slurry was then dewatered at 1100 rpm and 600 G for 30 minutes. The slurry was extremely good, having a specific cake resistance of $1.7 \times 10^9$ m/kg and the moisture content of the filtered crystals was 38 wt. %.

EXAMPLE 5

Using a 700-liter crystallizer equipped with a stirring equipment and a jacket, 25 kg of wet crystals of APM hydrochloride were dissolved in 300 liters of water previously warmed to 35° C. With stirring, 5 liters of 15 wt. % $Na_2CO_3$ aqueous solution was added thereto to give a pH of 2.5. After this solution was heated to 60° C., 29 liters of 15 wt. % $Na_2CO_3$ aqueous solution was further added thereto to give a pH of 4.9. This solution was heated to 65.5° C. and, with stirring, cooling water at −5° C. was introduced into the jacket and stirring crystallization was continued overnight under these conditions. The slurry thus obtained had a specific cake resistance of $4.0 \times 10^{10}$ m/kg.

This solution was dewatered in a centrifugal separator having a diameter of 4.7 inches at 3800 rpm for 5 minutes, and the moisture content thereof was 50 wt. %. 35 kg of the thus obtained crude wet crystals were again dissolved in 300 liters of water previously heated to 65° C. The resulting solution contained 5.0 g/dl of α-APM. This was transferred into the same cylindrical jacketed crystallizer having an inner diameter of 400 mm and a total length of 3000 mm as used in Example 4, and cooling water at −5° C. was introduced into the jacket for 3.5 hours. The bottom of the crystallizer was opened and the contents were transferred into another crystallizer equipped with a stirring equipment.

This slurry was continuously cooled overnight with stirring until the temperature thereof became 3° C. The bottom of the crystallizer was opened and the crystals were removed. No scaling on the inner wall of the crystallizer was observed and the crystal slurry was easily removed. 330 liters of the slurry thus obtained were subjected to solid-liquid separation in a centrifugal separator having a diameter of 36 inches and a volume of 92 liters, whereupon only 3 minutes were needed for charging the slurry into the separator. The slurry was then dewatered therein at 1100 rpm and 600 G for 30 minutes.

The slurry was extremely good, having a specific cake resistance of $2.7 \times 10^8$ m/kg and the moisture content of the obtained crystals was 28 wt. %.

EXAMPLE 6

1050 ml of an aqueous solution of α-APM hydrochloride were put in the same apparatus as used in Example 2, and 28 wt. % $NH_4OH$ was added thereto with stirring at 200 rpm at 27° C. to give a pH of 2.5. The solution was heated to 55° C. and 28 wt. % $NH_4OH$ was added thereto to give a pH of 4.9. The crystals formed were taken out in the same manner as in Example 1.

A portion (28 g) of the α-APM crystals formed was dissolved in 365 ml of deionized water and the resulting solution was added to the neutralized liquid to obtain an aqueous solution containing 5.2 g/dl of α-APM. The aqueous solution was heated to 68° C. and stirring was stopped. Then, cooling water of 5° C. was introduced into the jacket. Cooling was continued for one hour without stirring, then stirring was effected at 200 rpm, and cooling was thus continued with stirring until the inner temperature became 7° C. The slurry thus obtained was dewatered in a centrifugal separator having a diameter of 4.7 inches at 3800 rpm for 5 minutes.

The slurry was extremely good, having a specific cake resistance of $2.4 \times 10^9$ m/kg and the moisture content of the obtained crystals were 35 wt. %.

EXAMPLE 7

700 ml of an aqueous solution of α-APM hydrochloride were put in the same apparatus as used in Example 2, and 28 % $NH_4OH$ was added thereto with stirring at 200 rpm at 27° C. to give a pH of 2.5. The solution was heated to 55° C. and 28 wt. % $NH_4OH$ was added thereto to provide a pH of 4.9.

56 g of the α-APM crystals obtained in the same manner as in Example 1 were dissolved in 730 ml of deionized water and the resulting solution was added to the neutralized liquid to obtain an aqueous solution containing 4.9 g/dl of α-APM. The aqueous solution was heated to 68° C. and stirring was stopped. Then, cooling water at 5° C. was introduced into the jacket to conduct static crystallization. Cooling was continued for one hour without stirring, then stirring was effected at 200 rpm, and cooling was thus continued with stirring until the inner temperature became 7° C. The slurry thus obtained was easily separated by solid-liquid separation and was extremely good, having a specific cake resistance of $1.1 \times 10^9$ m/kg and the moisture content of the obtained crystals were 34 wt. %.

EXAMPLE 8

This demonstrates a 30-liter scale experiment. 1200 g of α-APM hydrochloride were put in 30 liter of water and dissolved with stirring at 30. C. While still stirring, 155 ml of 24 wt. % $Na_2CO_3$ aqueous solution was added to the solution to give a pH of 2.5. Then, the solution was heated to 50° C. 595 ml of 24 wt. % $Na_2CO_3$ aqueous solution was again added thereto to give a final pH of 4.9. The α-APM concentration in the neutralized liquid was 2.2 wt. %, and the NaCl concentration therein was 0.76 wt. %.

While maintaining the temperature at 50° C., the neutralized liquid was subjected to Ruth's reverse osmotic filtration. A spiral model Ruth's reverse osmotic membrane module manufactured by Teijin Engine-ring Co. (membrane area 2.4 m²) was used as the osmotic membrane for the filtration. The neutralized liquid as stocked in a stock tank was fed to the membrane module at an operating pressure of 14 kgf.cm$^{-2}$ and was subjected to batchwise desalting in such a way that the liquid which passed through the membrane was taken out of the system while the liquid not passed tnerethrough was returned back to the stock tank. At the point when the liquid amount in the stock tank became 1/1.5 of the initial amount, 10 liters of water was added thereto so that the whole amount was again made to be 30 liters. Thereafter the dialysis filtration was further effected in the same manner. 55% of the NaCl initially existing in the neutralized liquid was removed. The recovery of α-APM was 96%. The volume of the liquid after the Ruth's reverse osmotic filtration treatment was 20 liters, which had an α-APM concentration of 3.2 wt. % and an NaCl concentration of 0.51 wt. %.

The desalted liquid thus obtained was put in a container having a diameter of 350 mm and heated to 65° C. Using cooling water at 5° C., this was subjected to static crystallization without stirring for 2 hours. The content in the container became almost wholly a sherbet-like phase. This was stirred with a stirrer for one hour and cooled to a final temperature of 5° C. The crystal slurry thus obtained had a specific cake resistance of $1.5 \times 10^9$ m/kg. This was dewatered in a centrifugal separator having a diameter of 4.7 inches at 3800 rpm for 5 minutes to obtain wet crystals. The crystals had a water content of 53 wt. %. The solid-liquid separatability of the slurry was extremely good.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method of preparing α-L-aspartyl-L-phenylalanine methyl ester, comprising the steps of:
   (1) neutralizing an acid addition salt of α-L-aspartyl-L-phenylalanine methyl ester with a base to the isoelectric point of said ester in an aqueous medium, wherein (a) the concentration of said α-L-aspartyl-L-phenylalanine methyl ester in said medium is from 3 to 10 wt. % at the end of said neutralizing step, and (b) said neutralizing step is conducted to a pH of about 2.5 and a temperature of 40°0 C. or lower and thereafter neutralizing is continued with or after heating said medium to a temperature of from 50° to 80° C. with stirring, and
   (2) cooling said neutralized medium to precipitate crystals of α-L-aspartyl-L-phenylalanine methyl ester.

2. The method of claim 1, wherein said cooling step is conducted by stirring to obtain a fluid slurry.

3. The method of claim 1, wherein said cooling step is conducted with or without stirring to obtain a sherbet-like pseudosolid phase.

4. The method of claim 1, wherein a solution of or crystals of α-L-aspartyl-L-phenylalanine methyl ester are added before, during or after said neutralizing step, and then blended and dissolved, wherein the concentration of the α-APM in resulting solution is from 3 to 10 wt. %.

5. The method of claim 1, wherein said neutralized medium contains salts and is desalted by dialysis.

6. The method of claim 5, wherein 50 wt. % or more of said salts are removed from said neutralized medium.

7. The method of claim 1, wherein said acid addition salt is a hydrochloride salt.

8. The method of claim 1, further comprising
   (3) redissolving said crystals and then cooling the resulting solution to form a sherbet-like pseudosolid phase.

9. A method of preparing α-L-aspartyl-L-phenylalanine methyl ester, comprising the steps of:
   (1) neutralizing an acid addition salt of α-L-aspartyl-L-phenylalanine methyl ester with a base to the isoelectric point of said ester in an aqueous medium, wherein (a) the concentration of said α-L-aspartyl-L-phenylalanine methyl ester in said medium is from 3–10 wt. % at the end of said neutralizing step, and (b) a portion of said neutralizing step is conducted at a temperature of from 55°–80° C. with stirring and
   (2) cooling said neutralized medium to precipitate crystals of α-L-aspartyl-L-phenylalanine methyl ester.

10. The method of claim 9, wherein a portion of said neutralizing step is conducted at a temperature of 55°–65° C.

* * * * *